United States Patent
Jungbluth et al.

(10) Patent No.: US 8,125,219 B2
(45) Date of Patent: Feb. 28, 2012

(54) METHOD FOR DETERMINING AND EVALUATING EDDY-CURRENT DISPLAYS, IN PARTICULAR CRACKS, IN A TEST OBJECT MADE FROM AN ELECTRICALLY CONDUCTIVE MATERIAL

(75) Inventors: Matthias Jungbluth, Berlin (DE); Rolf Wilkenhöner, Kleinmachnow (DE)

(73) Assignee: Siemens Aktiengesellschaft, Munich (DE)

( * ) Notice: Subject to any disclaimer, the term of this patent is extended or adjusted under 35 U.S.C. 154(b) by 239 days.

(21) Appl. No.: 12/467,391

(22) Filed: May 18, 2009

(65) Prior Publication Data

US 2009/0289624 A1 Nov. 26, 2009

(30) Foreign Application Priority Data

May 20, 2008 (EP) .................................. 08009323

(51) Int. Cl.
*G01N 27/72* (2006.01)
(52) U.S. Cl. ........................ 324/239; 324/242
(58) Field of Classification Search ........... 324/239–243
See application file for complete search history.

(56) References Cited

U.S. PATENT DOCUMENTS

| | | | |
|---|---|---|---|
| 4,555,664 A | | 11/1985 | David et al. |
| 5,182,513 A * | | 1/1993 | Young et al. ................ 324/232 |
| 6,829,578 B1 * | | 12/2004 | Huang et al. ................ 704/211 |
| 7,049,811 B2 * | | 5/2006 | Schlicker et al. ............. 324/242 |
| 2002/0163333 A1 * | | 11/2002 | Schlicker et al. ............. 324/242 |
| 2006/0001420 A1 * | | 1/2006 | Beck et al. .................... 324/240 |

FOREIGN PATENT DOCUMENTS

| | | |
|---|---|---|
| DE | 4201502 A1 | 7/1993 |
| EP | 0165761 A2 | 12/1985 |

OTHER PUBLICATIONS

Nascimento et al., On the Learning Mechanism of Adaptive Filters, IEEE Transactions on Signal Processing, vol. 48, No. 6 (Jun. 2000).*
Lo et al., Adaptive Neural Filters with Fixed Weights, Proceedings of International Joint Conference on Neural Networks (Aug. 2007).*

* cited by examiner

*Primary Examiner* — Melissa Koval
*Assistant Examiner* — Daniel Miller

(57) ABSTRACT

A method for determining and evaluating eddy-current displays, in particular cracks, in a test object made from an electrically conductive material is provided. The method uses the following steps, applying an alternating electromagnetic field of a predetermined constant or variable frequency to the test object, detecting the eddy currents induced in the test object along predetermined parallel measuring tracks, providing eddy-current signals each eddy-current signal is assigned to a measuring track, conditioning the eddy-current signals and providing conditioned measured variables, interpreting the conditioned measured variables using a predetermined evaluation algorithm, and providing synthetic crack signals.

17 Claims, 2 Drawing Sheets

METHOD FOR DETERMINING AND EVALUATING EDDY-CURRENT DISPLAYS, IN PARTICULAR CRACKS, IN A TEST OBJECT MADE FROM AN ELECTRICALLY CONDUCTIVE MATERIAL

CROSS REFERENCE TO RELATED APPLICATIONS

This application claims priority of European Patent Office application No. 08009323.0 EP filed May 20, 2008, which is incorporated by reference herein in its entirety.

FIELD OF INVENTION

The invention relates to a method for determining and evaluating eddy-current displays, in particular cracks, in a test object made from an electrically conductive material.

BACKGROUND OF INVENTION

Non-destructive methods are required in the case of numerous material tests. Examples are the surfaces of components made from metal frequently exposed to an environment that effects corrosion, oxidation, diffusion and further ageing processes. Cracks can also be caused in the surface of the component by mechanical stresses.

This also applies, for example, to the moving and guide blades of a gas turbine that are exposed, in particular, to crack formation at their surface owing to mechanical and thermal loads. Non-destructive test methods are required in order to be able to check the current state of such a blade wheel.

SUMMARY OF INVENTION

Suitable non-destructive test methods can be carried out by applying the eddy-current principle. In this case, the test object is exposed to an alternating electromagnetic field whose frequency can be set. Eddy currents are thereby induced in the test object. The electromagnetic field, or the induced voltage thereof, produced by the eddy-currents is detected. The amplitude and the phase angle of the induced voltage can be determined in this case.

The eddy-current method can be used in order to be able to determine cracks in the surface of the component. The crack depth can also be determined in principle with the aid of the eddy-current method. However, it is not known how it is possible to distinguish between single cracks and a number of closely adjacent cracks.

It is an object of the invention to provide an improved method for determining and evaluating one or more eddy-current displays in particular cracks, in an electrically conductive component that also enables reliable distinction between a single crack and a number of adjacent cracks.

This object is achieved by the subject matter in accordance with the claims.

The inventive method for determining and evaluating eddy-current displays, in particular cracks, in a test object made from an electrically conductive material has the following steps:— applying an alternating electromagnetic field of a predetermined constant or variable frequency to the test object, detecting the eddy-currents induced in the test object along predetermined parallel measuring tracks on a surface portion of the test object, providing eddy-current signals, each eddy-current signal being assigned to a measuring track conditioning the eddy-current signals and providing conditioned measured variables as a function of the measuring track, the frequency and a position along the measuring track, interpreting the conditioned measured variables with the use of conditioned measured variables of at least one adjacent measuring track, and providing synthetic crack signals with corrected amplitude and/or track position by comparison with the conditioned measured variables.

The core of the invention resides in the fact that the surface or a surface portion of the test object is scanned along parallel measuring tracks. A surface or a surface portion of the test object is thereby effectively scanned. In this case, the eddy-currents induced in the test object are detected. The detected measured data are combined with the measured data of adjacent measuring tracks. It is possible in this way to correct the detected measured data of a measuring track by taking account of measured data of adjacent measuring tracks. It is likewise possible for ambiguous measured data of a measuring track to be interpreted unambiguously by taking account of the measured data of adjacent measuring tracks.

The voltage induced by the eddy-currents is advantageously detected. In this case the amplitude and phase of the voltage induced by the eddy-currents can be detected. Cracks in the test object lead to locally different electrical properties, for example a lower electrical conductivity than the material of the test object. The induced voltage is influenced in this way and the cracks are detected.

The conditioned measured variables are preferably interpreted on the basis of a predetermined evaluation algorithm.

For example, the evaluation algorithm is based on an empirically determined set of rules. To this end, it is possible, in particular, to carry out reference measurements on copies of the test object with known properties, and to generate calibration functions there from.

Alternatively or in addition, the evaluation algorithm can be based on a self learning method, in particular with the use of a neural network.

In terms of measurement technology, a multichannel sensor is used to detect the eddy-currents, each channel being assigned a measuring track. The multichannel sensor enables a variety of measurements to be taken simultaneously.

In particular, the parallel measuring tracks can be scanned simultaneously.

As an alternative thereto, a single sensor can be used to detect the eddy-currents, the parallel measuring tracks being scanned sequentially.

By way of example, the alternating electromagnetic field is applied with a plurality of discrete frequencies to the test object. Since specific properties of the alternating electric field are functional of the frequency, it is thereby possible to obtain additional information relating to the test object.

Likewise, the alternating electromagnetic field can be applied with a continuous frequency spectrum to the test object. Again, the frequency spectrum has a characteristic structure and permits physical properties of the test object to be inferred.

The synthetic crack signals are chiefly used to determine geometric properties of one or more cracks.

It is provided, in particular, that the synthetic crack signals are used to determine the depth of one or more cracks. The depth of the crack is decisive in many instances as to whether the test object must be renewed or repaired.

Furthermore, the eddy-current signals can be used to determine the electrical conductivity. Again, information relating to the geometric structure of the cracks can be obtained from the electrical conductivity.

In the preferred embodiment of the invention, mechanical guide means are used in order to establish the movement of the eddy-current sensor along the measuring tracks on the surface portion of the test object. The method is thereby reproducible. Particularly in the case of the application of a single sensor, mechanical guidance is advantageous for ensuring the defined track spaces. Reference measurements can be carried out in order, for example, to determine the evaluation algorithm or calibration curves.

It is preferable to this end that the mechanical guide means have been or are adapted to the geometric shape of the test object.

In particular, the method is provided for determining and evaluating cracks on and/or in the region of the surface of the test object. The surface of the test object is particularly exposed during operation to the mechanical and the chemical loads.

Finally, it is provided to use the method to determine and evaluate cracks below the surface of the test object in the measuring range of the alternating electromagnetic field. The cracks below the surface of the test object also influence electrical properties thereof, and thus the eddy-currents.

Further features, advantages and particular embodiments of the invention are the subject matter of the subclaims.

BRIEF DESCRIPTION OF THE DRAWINGS

The method in accordance with the invention is explained in more detail below in the description of the figures with the aid of preferred embodiments and with reference to the attached drawings, in which.

DETAILED DESCRIPTION OF INVENTION

Figure 1:
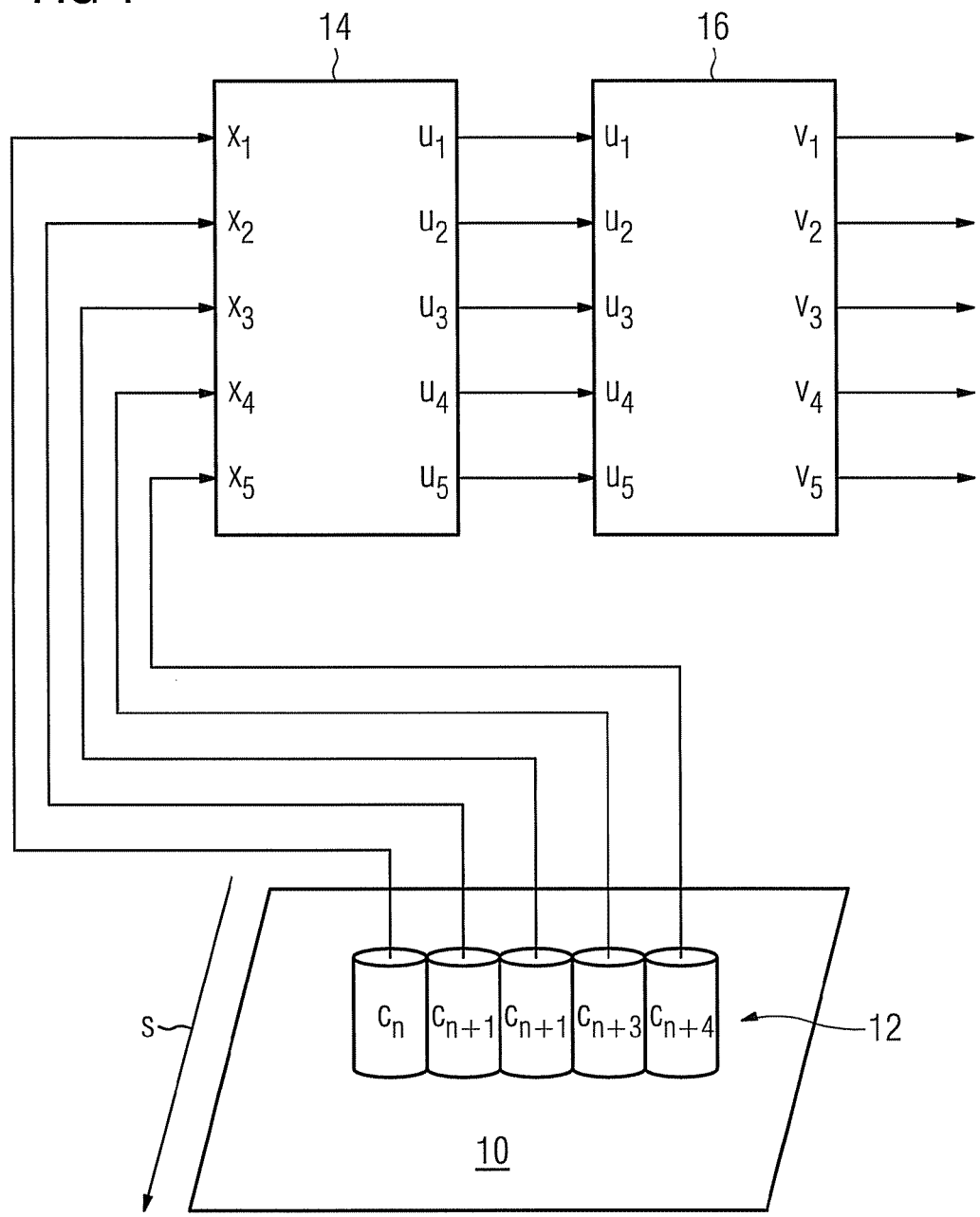
FIG. 1 shows a schematic view of a detection and evaluation of eddy-current signals in accordance with the preferred embodiment of the inventive method.

FIG. 1 shows a schematic view of a detection and evaluation of eddy-current signals $x_1$, $x_2$, $x_3$, $x_4$ and $x_5$ on a surface portion 10 of a test object in accordance with the preferred embodiment of the inventive method. An eddy-current sensor 12 is used to scan the surface portion 10 of the test object.

The test object is exposed to an alternating electromagnetic field with a frequency f that can be set. One or more specific frequencies f can be provided. Likewise, a continuous frequency spectrum with predetermined cutoff frequencies can be used. Eddy currents are induced in the test object by the alternating electromagnetic field. The electromagnetic field or the induced voltage thereof, produced by the eddy-currents, is detected by the eddy-current sensor 12.

The eddy-current sensor 12 can be formed either as a single sensor or as a multichannel sensor. In the case of this particular embodiment, the eddy-current sensor 12 is designed as a multichannel sensor and comprises five channels $c_n$, $c_{n+1}$, $c_{n+2}$, $c_{n+3}$ and $c_{n+4}$. Each single sensor is assigned a measuring track by the movement of the eddy-current sensor 12 along the movement direction. The measuring tracks are arranged parallel to one another on the surface portion 10. Likewise, each of the channels $c_n$, $c_{n+1}$, $c_{n+2}$, $c_{n+3}$ and $c_{n+4}$ is respectively assigned to a measuring track.

In the case of the alternative use of the single channel sensor, the measuring tracks on the surface portion 10, which run in parallel, are scanned sequentially with the aid of the same sensor.

The eddy-current signals $x_1$, $x_2$, $x_3$, $x_4$ and $x_5$ of the individual channels $c_n$, $c_{n+1}$, $c_{n+2}$, $c_{n+3}$ and $c_{n+4}$ are processed in a signal conditioning 14 and subsequently in a logic combination 16.

Firstly, the eddy-current signals $x_1$, $x_2$, $x_3$, $x_4$ and $x_5$ of the individual channels $c_n$, $c_{n+1}$, $c_{n+2}$, $c_{n+3}$ and $c_{n+4}$ are subjected to the signal conditioning 14. During the signal conditioning 14, conditioned measured variables $u_1$, $u_2$, $u_3$, $u_4$ and $u_5$ are generated for each channel $c_n$, $c_{n+1}$, $c_{n+2}$, $c_{n+3}$ and $c_{n+4}$. The conditioned measured variables $u_1$, $u_2$, $u_3$, $u_4$ and $u_5$ are functions of the channel $c_n$, $c_{n+1}$, $c_{n+2}$, $c_{n+3}$ and $c_{n+4}$, the frequency f and a measuring position s. The measuring position s defines a point on the respective measuring track.

The signal conditioning 14 of the eddy-current signals $x_1$, $x_2$, $x_3$, $x_4$ and $x_5$ is performed separately for each channel $c_n$, $c_{n+1}$, $c_{n+2}$, $c_{n+3}$ and $c_{n+4}$ and for each frequency f.

In the subsequent logic combination 16, the conditioned measured variables $u_1$, $u_2$, $u_3$, $u_4$ and $u_5$ are interpreted using predetermined criteria.

Here, for each measuring position s the value of one or more selected conditioned measured variables $u_1$, $u_2$, $u_3$, $u_4$ and $u_5$ is compared with the adjacent positions. Moreover, the value of the selected conditioned measured variables $u_1$, $u_2$, $u_3$, $u_4$ and $u_5$ can be compared with those of the adjacent positions for various frequencies f.

Synthetic crack signals $v_1$, $v_2$, $v_3$, $v_4$ and $v_5$ are generated in this case by applying the evaluation algorithm on the basis of an empirically determined set of rules or via a self learning approach. The assignment to the test track $c_n$ and the amplitude are corrected in the synthetic crack signals $v_1$, $v_2$, $v_3$, $v_4$ and $v_5$. The crack signals $v_1$, $v_2$, $v_3$, $v_4$ and $v_5$ corrected in this way improve the statement relating to position and number of the cracks and can be used to determine the depth of the crack.

A linear representation or two dimensional representation of the eddy-current signals $x_1$, $x_2$, $x_3$, $x_4$ and $x_5$ is generated by scanning the surface portion 10 of the test object. The eddy-current signals $x_1$, $x_2$, $x_3$, $x_4$ and $x_5$ are therefore a function of the position s along the measuring track, or a position on the surface portion 10.

A mechanical guide device is provided in order to move the eddy-current sensor 12 along the predetermined measuring track reproducibly.

The use of a plurality of frequencies f makes possible additional information relating to the properties of the crack, since a plurality of electromagnetic variables are dependent on the frequency. Various frequencies f can be applied to the test object simultaneously or sequentially.

Figure 2:
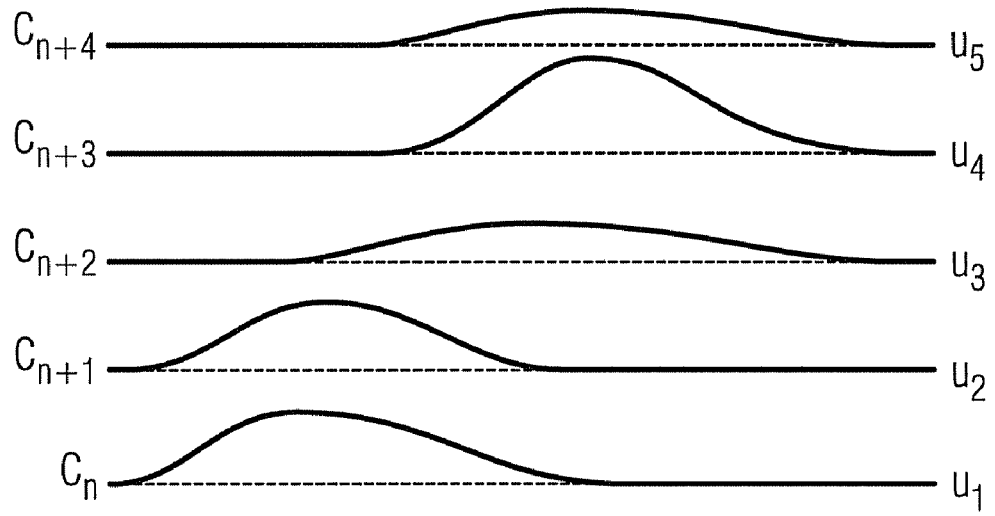
FIG. 2 shows a schematic exemplary graphic illustration of conditioned measurement signals after signal conditioning in accordance with the preferred embodiment of the inventive method before the application of the evaluation algorithm.

FIG. 2 shows a schematic exemplary graphic illustration of the conditioned measured variables $u_1$, $u_2$, $u_3$, $u_4$ and $u_5$ after the signal conditioning 12 and before the logic combination 16 in accordance with the preferred embodiment of the inventive method. The conditioned measured variables $u_1$, $u_2$, $u_3$, $u_4$ and $u_5$ emerge in each case from the corresponding eddy-current signals $x_1$, $x_2$, $x_3$, $x_4$ and $x_5$.

The signal conditioning 14 of the eddy-current signals $x_1$, $x_2$, $x_3$, $x_4$ and $x_5$ are performed separately for each channel $c_n$, $c_{n+1}$, $c_{n+2}$, $c_{n+3}$ and $c_{n+4}$ and for each frequency f. The corresponding conditioned measured variables $u_1$, $u_2$, $u_3$, $u_4$ and $u_5$ are generated for each channel $c_n$, $c_{n+1}$, $c_{n+2}$, $c_{n+3}$ and $c_{n+4}$ during the signal conditioning 14. The resulting conditioned measured variables $u_1$, $u_2$, $u_3$, $u_4$ and $u_5$ are functions of the channel $c_n$, $c_{n+1}$, $c_{n+2}$, $c_{n+3}$ and $c_{n+4}$, the frequency f and a measuring position s.

Figure 3:
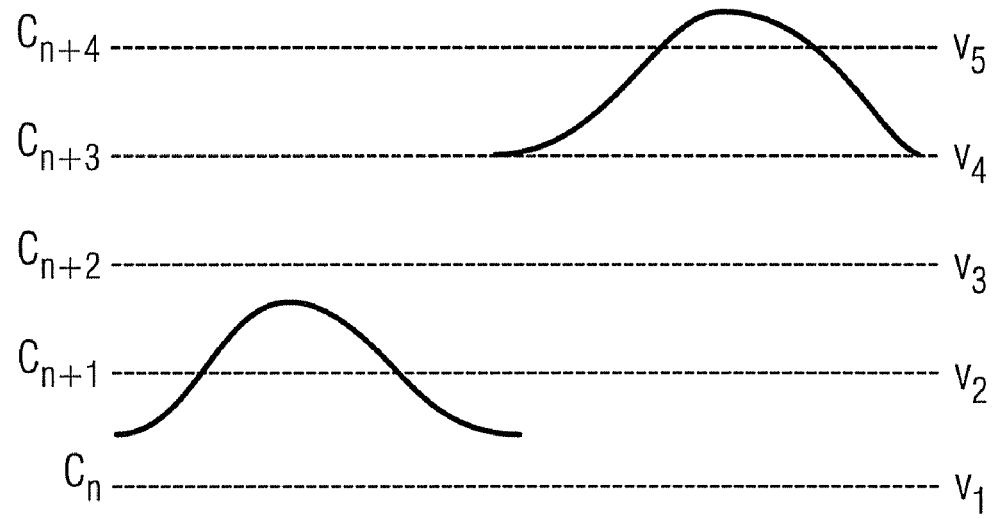
FIG. 3 shows a schematic exemplary graphic illustration of synthetic crack signals after a logic combination in accordance with the preferred embodiment of the inventive method after the application of the evaluation algorithm.

FIG. 3 shows a schematic exemplary graphic illustration of the synthetic crack signals $v_1$, $v_2$, $v_3$, $v_4$ and $v_5$ after the logic combination 16 in accordance with the preferred embodiment of the method. The synthetic crack signals $v_1$, $v_2$, $v_3$, $v_4$ and $v_5$ emerge from the conditioned measured variables $u_1$, $u_2$, $u_3$, $u_4$ and $u_5$. The corresponding conditioned measured variable $u_3$ and at least also the adjacent conditioned measured variables $u_2$ and $u_4$ are used in determining the synthetic crack signal $u_3$. The evaluation of the adjacent conditioned measured variables $u_1$ and $u_5$ leads to the result of a single signal positioned between the channels.

The inventive method is a particularly efficient method both for establishing cracks in the surface of the test object, and for evaluating them. Moreover, further geometric properties of the cracks can be determined by establishing whether there is a single crack or two or more cracks lying next to one another.

The invention claimed is:

1. A method for determining and evaluating eddy-current displays, in particular cracks, in a test object made from an electrically conductive material, comprising:

applying an alternating electromagnetic field of a predetermined constant frequency or a predetermined variable frequency to the test object;

detecting a plurality of eddy-currents induced in the test object along a plurality of predetermined parallel measuring tracks on a surface portion of the test object;

providing a plurality of eddy-current signals, each eddy-current signal is assigned to a measuring track;

separately conditioning in a signal conditioning device each of the plurality of the eddy-current signals and providing a corresponding plurality of separately conditioned measured variables, each of the plurality of separately conditioned measured variables determined as a function of the measuring track, the frequency, and a position along the measuring track;

interpreting in a signal combination device each of the plurality of separately conditioned measured variables, wherein the interpreting includes for each separately conditioned measured variable using at least one other separately conditioned measured variable having an adjacent measuring track for an interpretation, wherein the interpreting comprises comparing a value of a conditioned measured variable assigned to a respective measuring track relative to respective values of conditioned measured variables assigned to measuring tracks located adjacent to the respective measuring track; and as a result of the interpreting, generating a plurality of synthetic crack signals, wherein the synthetic crack signals are configured to correct respective amplitudes and respective spatial locations of the synthetic crack signals relating to the respective measuring tracks, wherein the synthetic crack signals are configured to synthesize into at least a single signal, information derived from comparing the value of the conditioned measured variable assigned to the respective measuring track relative to respective values of conditioned measured variables assigned to measuring tracks located adjacent to the respective measuring track.

2. The method as claimed in claim 1, wherein an amplitude and a phase of the plurality of eddy-currents induced by the alternating magnetic field are detected.

3. The method as claimed in claim 1, wherein the plurality of conditioned measured variables are interpreted on the basis of a predetermined evaluation algorithm.

4. The method as claimed in claim 3, wherein the predetermined evaluation algorithm is based on an empirically determined set of rules.

5. The method as claimed in claim 4, wherein the evaluation algorithm is based on a self learning method using a neural network.

6. The method as claimed in claim 1, wherein a multichannel sensor is used to detect the plurality of eddy-currents, each channel of the multichannel sensor is assigned to a measuring track.

7. The method as claimed in claim 6, wherein the plurality of predetermined parallel measuring tracks are scanned simultaneously with the multichannel sensor.

8. The method as claimed in claim 1,
wherein a single sensor is used to detect the plurality of eddy-currents, and
wherein the plurality of predetermined parallel measuring tracks are scanned sequentially using the single sensor.

9. The method as claimed in claim 1, wherein the alternating electromagnetic field is applied with a plurality of discrete frequencies to the test object.

10. The method as claimed in claim 1, wherein the alternating electromagnetic field is applied with a continuous frequency spectrum to the test object.

11. The method as claimed in claim 1, wherein the plurality of synthetic crack signals are used to determine a plurality of geometric properties of a crack.

12. The method as claimed in claim 1, wherein the plurality of synthetic crack signals are used to determine a depth of a crack.

13. The method as claimed in claim 1, wherein the plurality of eddy-current signals are used to determine an electrical conductivity.

14. The method as claimed in claim 6, wherein a mechanical guide is used in order to establish a movement of the multichannel sensor along the plurality of parallel measuring tracks on the surface portion.

15. The method as claimed in claim 14, wherein the mechanical guide is adapted to a geometric shape of the test object.

16. The method as claimed in claim 1, wherein the method is provided for determining and evaluating a plurality of cracks on and/or in a region of the surface portion.

17. The method as claimed in claim 1, wherein the method is provided for determining and evaluating a plurality of cracks below the surface portion.

* * * * *